(12) United States Patent
Calderon et al.

(10) Patent No.: US 7,534,888 B2
(45) Date of Patent: May 19, 2009

(54) OXYCODONE POLYMORPHS

(75) Inventors: Abram Calderon, West Lafayette, IN (US); Douglas Phillip Cox, Audubon, PA (US); Patrick Thomas Cyr, Wilmington, DE (US); Aeri Park, West Lafayette, IN (US)

(73) Assignee: Noramco, Inc., Athens, GA (US)

( * ) Notice: Subject to any disclaimer, the term of this patent is extended or adjusted under 35 U.S.C. 154(b) by 835 days.

(21) Appl. No.: 10/641,440

(22) Filed: Aug. 15, 2003

(65) Prior Publication Data

US 2007/0197572 A1 Aug. 23, 2007

Related U.S. Application Data

(60) Provisional application No. 60/403,826, filed on Aug. 15, 2002.

(51) Int. Cl.
    C07D 489/08 (2006.01)
    C07D 489/02 (2006.01)
(52) U.S. Cl. .......................................... 546/45; 546/46
(58) Field of Classification Search .................. 546/45, 546/46; 514/282
    See application file for complete search history.

(56) References Cited

U.S. PATENT DOCUMENTS 5,508,042 A * 4/1996 Oshlack et al. ............. 424/468
5,981,751 A * 11/1999 Mudryk et al. ................ 546/45

FOREIGN PATENT DOCUMENTS

DE 286 431 C 8/1915
DE 411 530 C 3/1925
EP 0 900 582 A 3/1999

OTHER PUBLICATIONS

M. Freund et al., "Über die Umwandlung von Thebain in Oxycodeinon und dessen Derivate", Journal fur Praktische Chemie, 1916, pp. 135-178.
R. Lutz, et al., "Reduction Studies in the Morphine Series. IX. Hydroxycodeinone", 1939, pp. 220-233.
M. Roulleau et al., "Cristallographie Chimique,-Influence du Champ Electrique Sur la Vitesse de Cristallisation du Salol" C.R. Acad. So. Paris, t. 265 (Oct. 30, 1967), pp. 961-964.
M. Sumwalt et al., The Respiratory Effects of Morphine, Codeine, and Related Substances VIII. The Effect of Substitutions on Carbon-$14^1$, 1941, pp. 229-245 iii-iv.
PCT International Search Report, dated Jan. 14, 2004, for PCT Int'l. Appln. No. PCT/US03/25778.
Budavari, S. et al., "The Merck Index, $12^{th}$ ed.", Merck Research Laboratories, Whitehouse Station, NJ 1996.
Caira, M.R., "Crystalline Polymorphism of Organic Compounds in Top. Curr. Chem.," Springer Verlag, Heidelberg, vol. 198, 1998.
Carelli, V., "L' Analisi Roentgenografica Nella Ricerca Tossicologica Di Alcaloidi E Sintetici Ad Azione Stupefacente", Farmaco Ed. Sci., vol. 11, pp. 317-335 1956.
Deutscher Apotheker Verlag, Stuttgart, "Deutsches Arzneibuch 1996, Monographien G-O", 1996.
Parfitt, K., "Martindale, The Complete Drug Reference, $32^{nd}$ ed.", Pharmaceutical Press, London 1999.

* cited by examiner

*Primary Examiner*—Charanjit S Aulakh
(74) *Attorney, Agent, or Firm*—Mary A. Appollina

(57) ABSTRACT

Oxycodone.HCl polymorph forms are disclosed which are useful as analgesic agents either in combination with or as replacements for oxycodone.

64 Claims, 10 Drawing Sheets

FIGURE 1. Oxycodone, 2-Theta
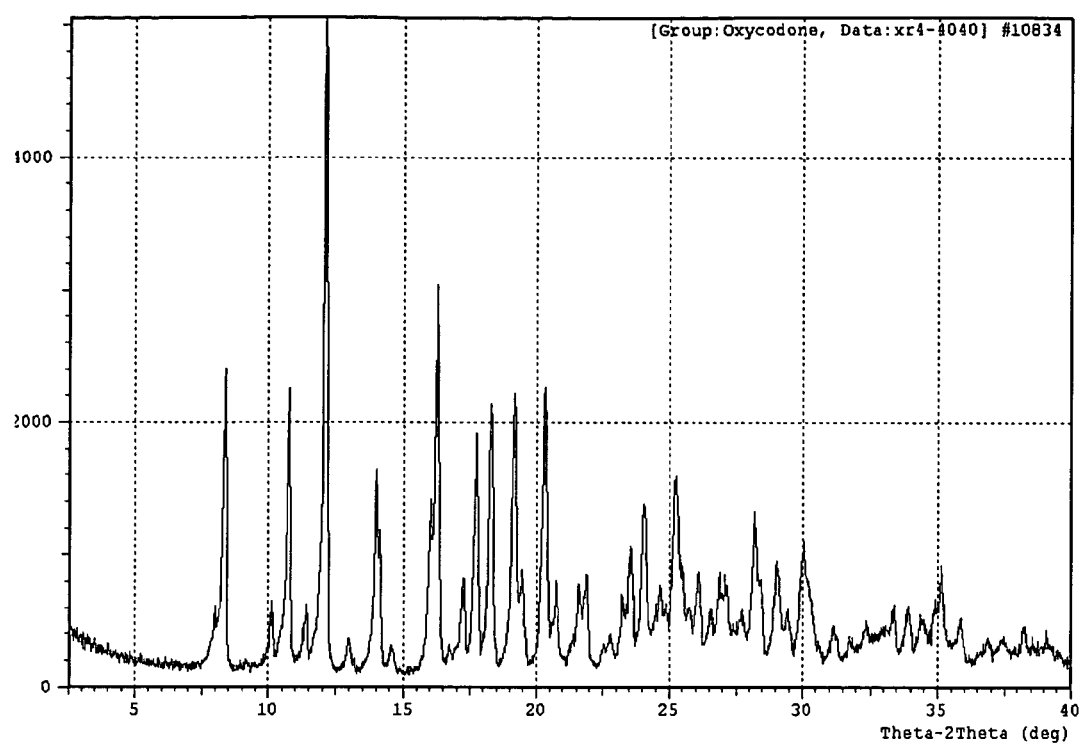

FIGURE 2  Form A, 2-Theta
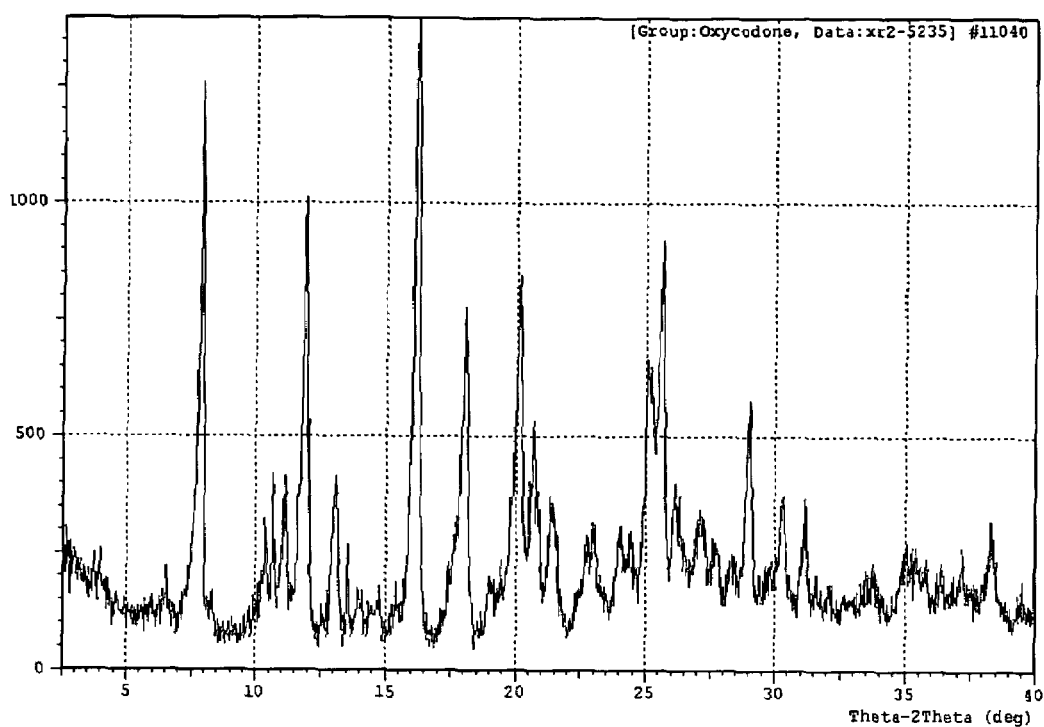

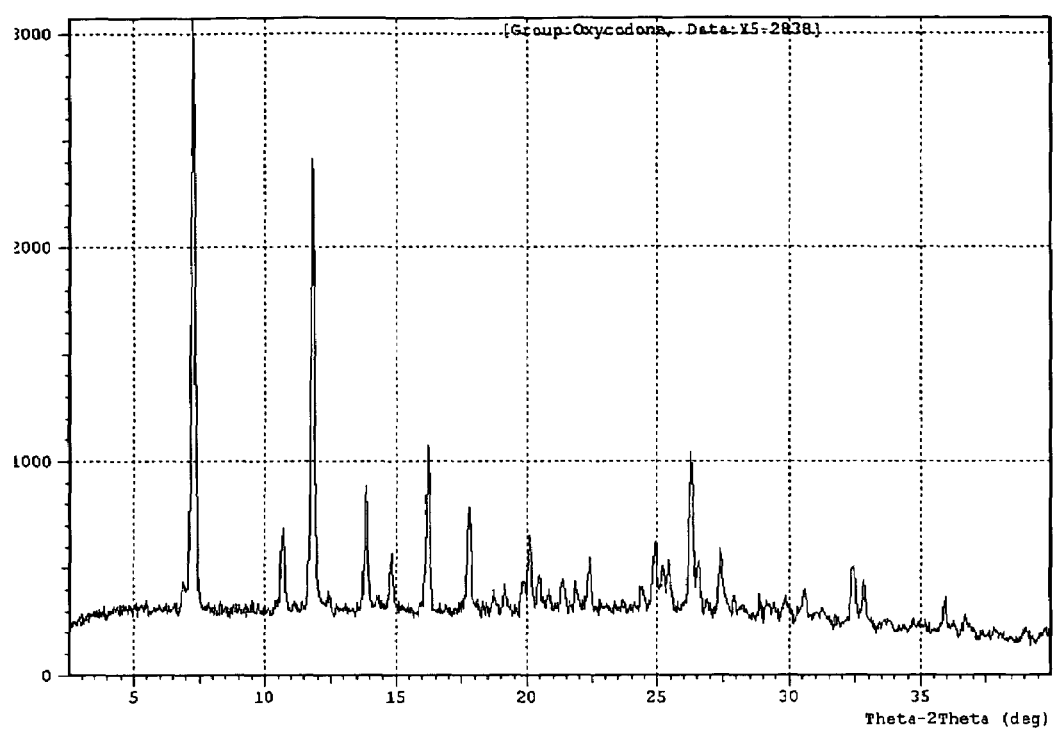
FIGURE 3. Form I, 2-Theta

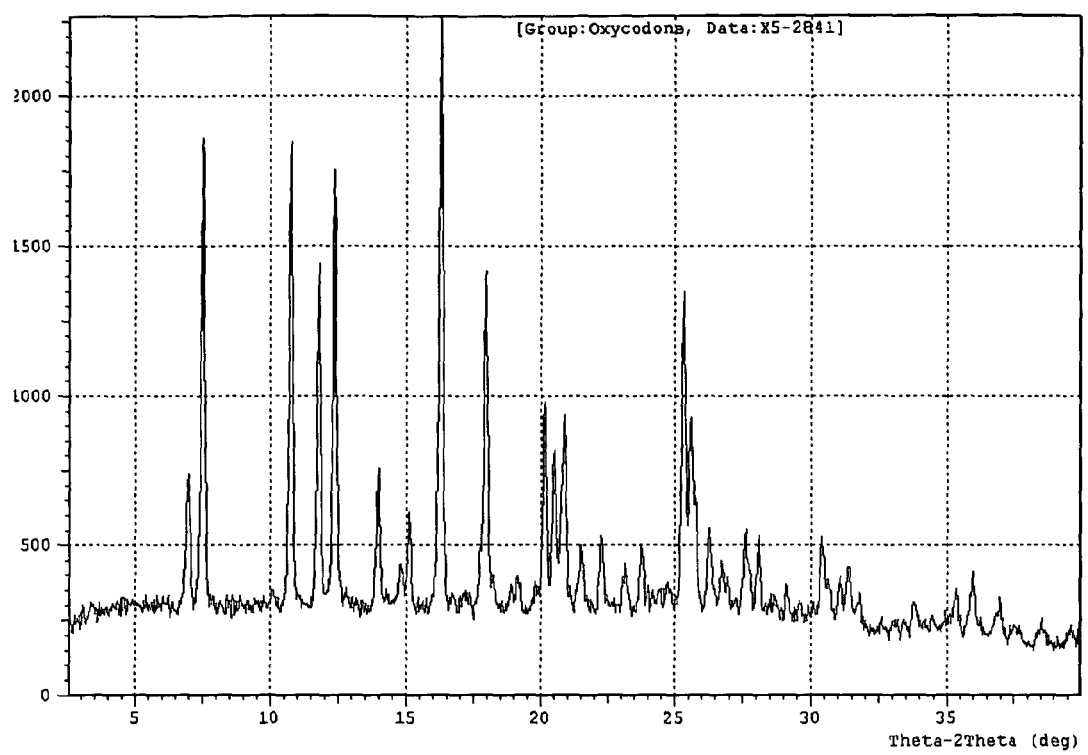
FIGURE 4. Form II, 2-Theta

FIGURE 5. Form III, 2-Theta
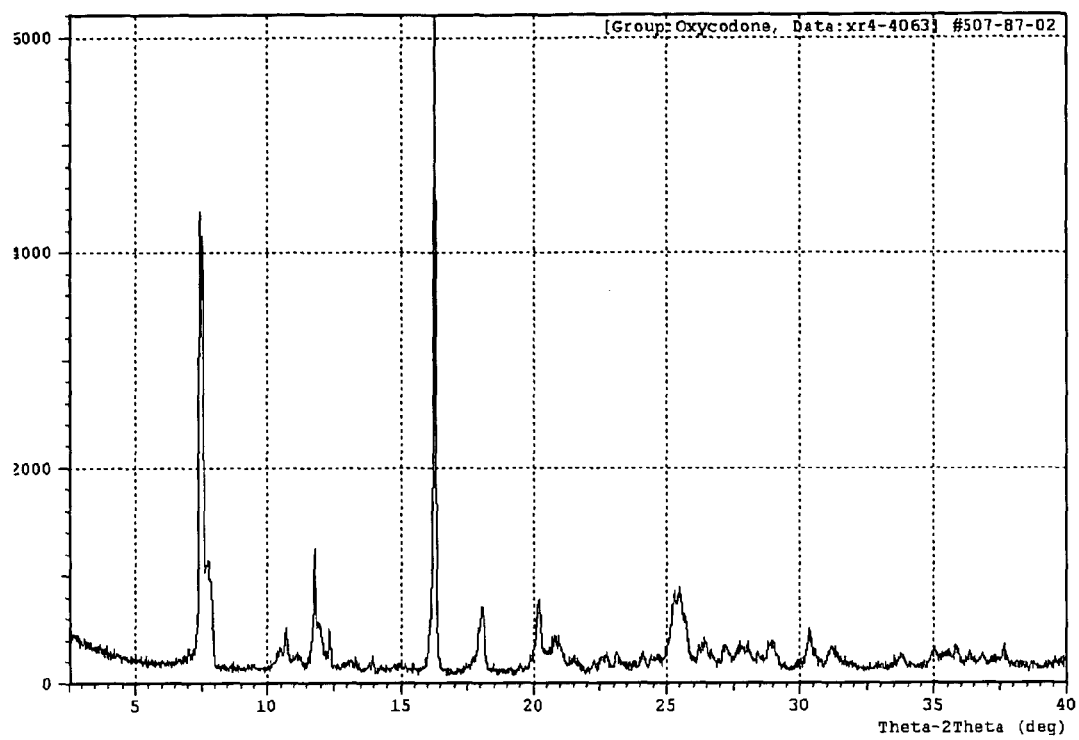

FIGURE 6. Form IV, 2-Theta
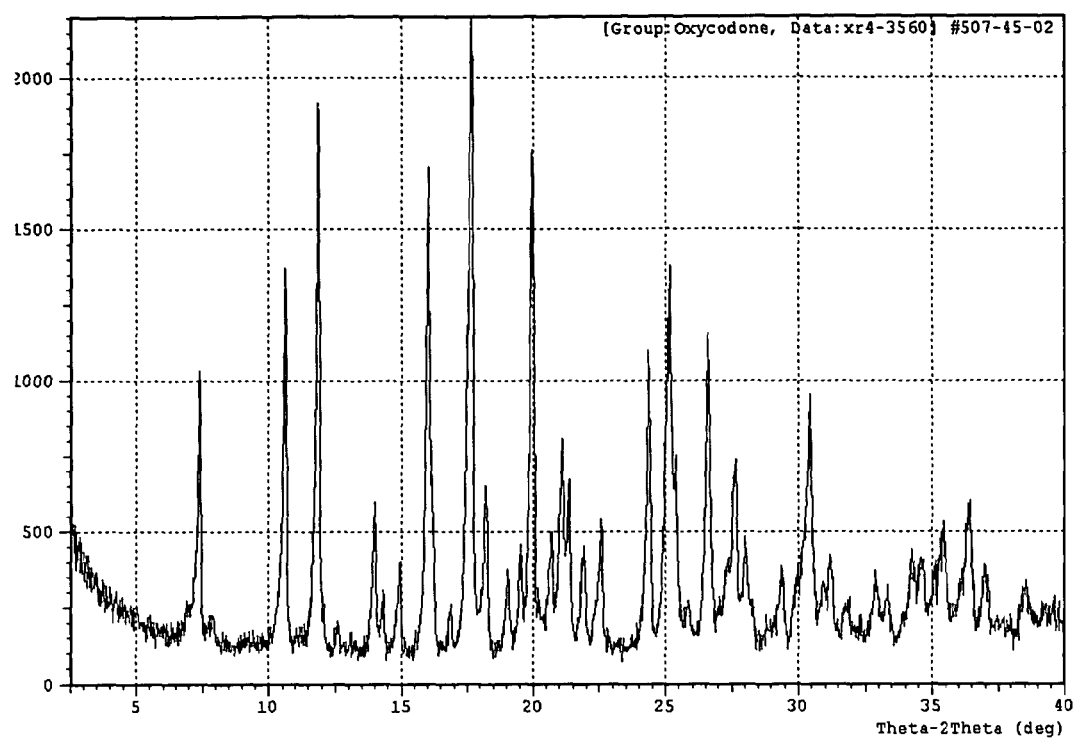

FIGURE 7. Form V, 2-Theta
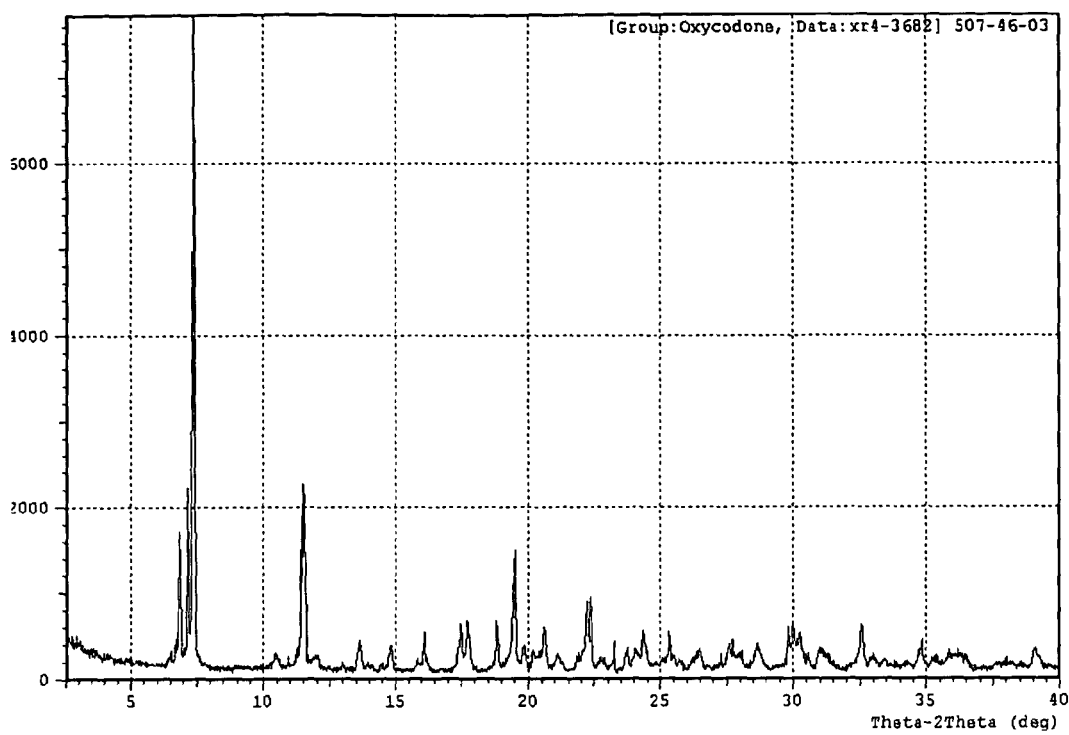

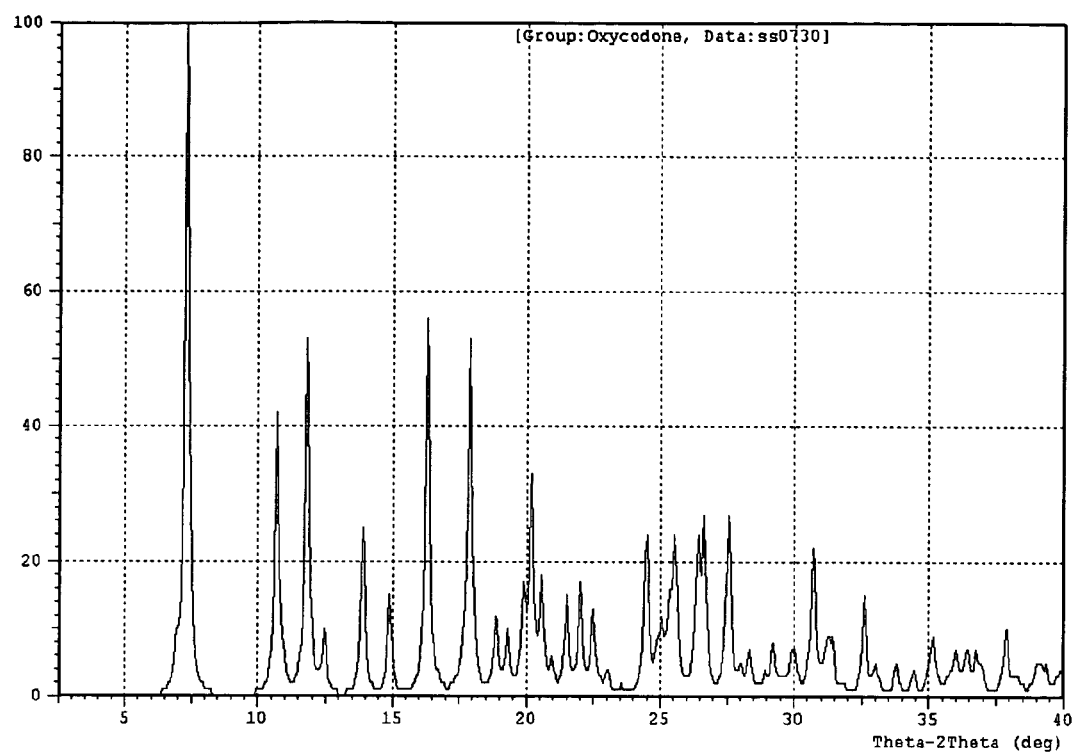
FIGURE 8. Form VI, 2-Theta

FIGURE 9. Form VII, 2-Theta
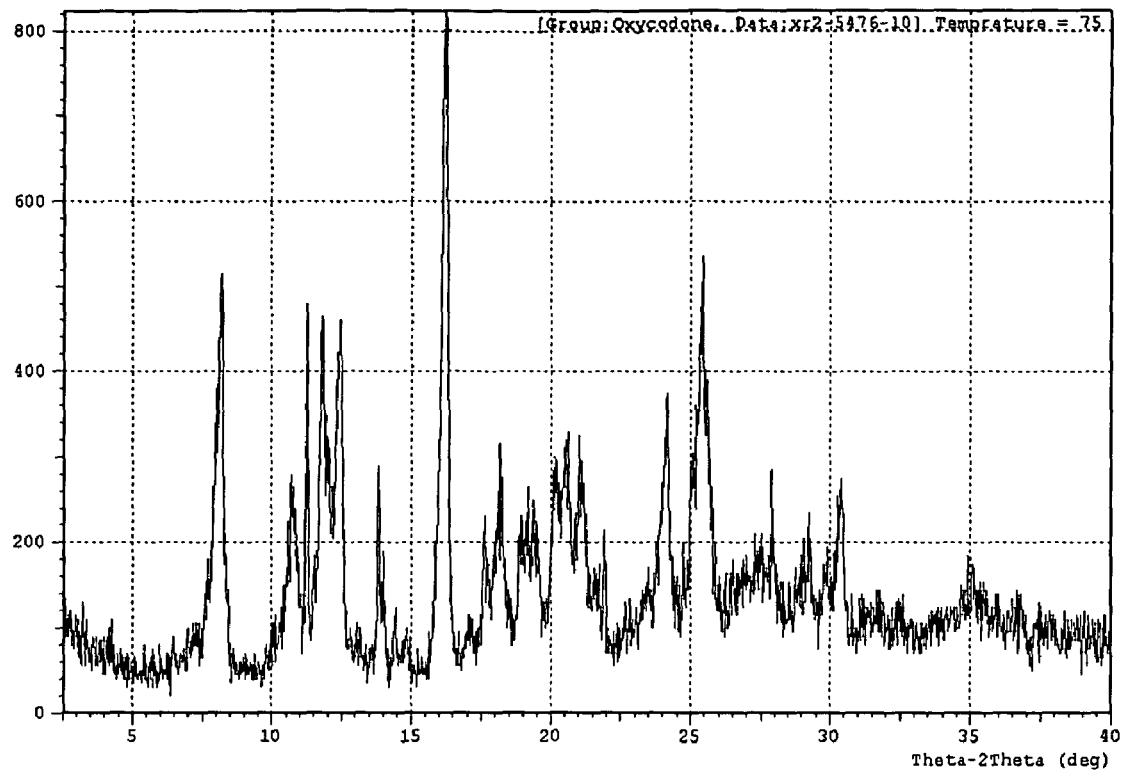

FIGURE 10. Form VIII, 2-Theta
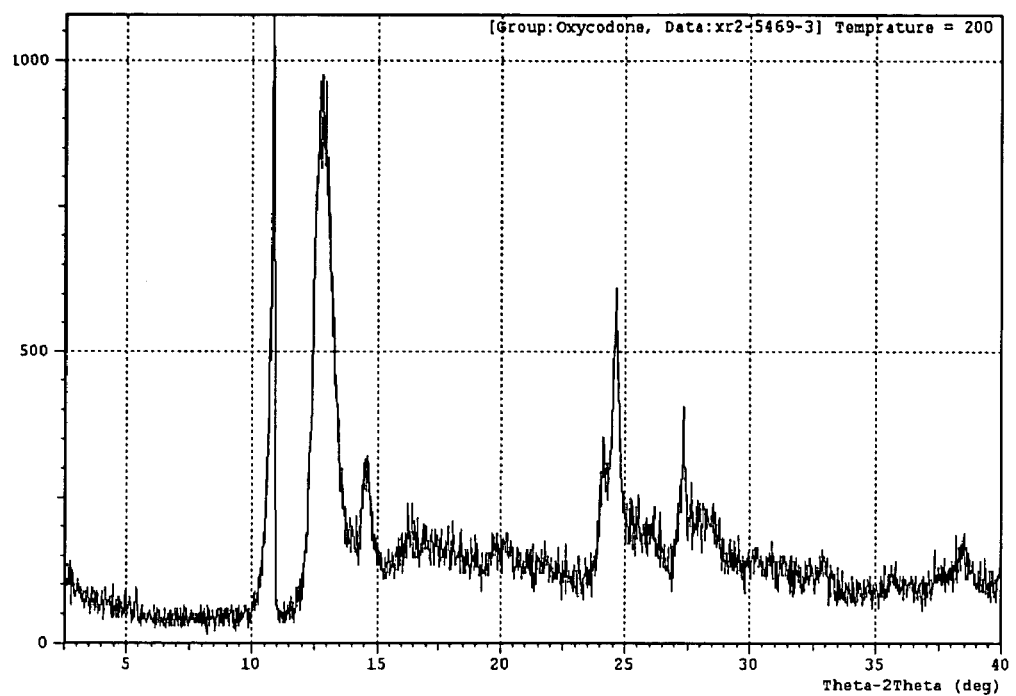

OXYCODONE POLYMORPHS

CROSS REFERENCE TO RELATED APPLICATIONS

This application claims benefit to U.S. provisional application Ser. No. 60/403,826, filed on Aug. 15, 2002.

BACKGROUND OF THE INVENTION

Oxycodone (4,5-epoxy-14-hydroxy-3-methoxy-17-methylmorphinan-6-one) is a well-known narcotic analgesic. The hydrochloride salt is commercially used in numerous products, such as Oxycontin, Tylox, and Percocet.

SUMMARY OF THE INVENTION

The present invention is directed to nine novel forms of oxycodone.HCl. These are identified herein as forms A and I-VIII. The known form of the oxycodone.HCl is referred to hereinafter as oxycodone.

DETAILED DESCRIPTION OF THE INVENTION

All nine forms are derived directly or indirectly from oxycodone and are characterized by physical data, most notable by their X-ray powder diffraction patterns expressed in terms of °2θ and the relative intensities of the X-ray diffraction peaks.

One aspect of the invention is the novel forms of oxycodone. Another aspect is processes to make these novel forms. Since these forms are essentially equally effective as oxycodone itself, they can be used instead of or in combination with oxycodone for its pharmacological effects. The novel forms may be produced and used as the pure form, or the forms may be produced and used in combination with other forms and/or oxycodone. Another aspect of the invention is compositions comprising therapeutically effective amounts of one or more of these novel forms, optionally in combination with oxycodone, and pharmaceutically acceptable carriers therefor. Another aspect is a method of providing an analgesic effect to a mammal, preferably a human, in need thereof which comprises administering to said mammal a therapeutic amount of one or more of a novel form of the invention, optionally in combination with oxycodone. Oxycodone, its therapeutic uses and doses ranges, modes of administration, etc. are all well known in the art.

By pure is meant that each form of the invention is about 90-100%, preferably 95-100%, more preferably 98-100% (wt./wt.) pure; e.g. free of other oxycodone forms, solvents, and/or other undesirable non-oxycodone impurities. A preferred polymorph of the invention is one which is free of other oxycodone forms, preferably 98-100% free.

The forms of the invention may be produced by a process which comprises:
1) dissolving oxycodone in a solvent which comprises water, an organic solvent such as dioxane or ethanol, or a combination of water and a lower alkanol which is ethanol, isopropanol, or butanol, optionally heating said solution as to 60° C., optionally stirring said solution, and optionally evaporating said solvent to precipitate the novel oxycodone form; or
2) heating Form A to 60-120° C.; or
3) heating oxycodone to 200° C.

Another embodiment of the invention is a form of oxycodone made by the process supra, more specifically a form made by a process such as recited in the examples.

BRIEF DESCRIPTION OF THE DRAWINGS

FIG. 1. is an X-ray powder diffraction pattern of oxycodone expressed in terms of °2θ.

FIG. 2. is an X-ray powder diffraction pattern of oxycodone form A expressed in terms of °2θ.

FIG. 3. is an X-ray powder diffraction pattern of oxycodone form I expressed in terms of °2θ.

FIG. 4. is an X-ray powder diffraction pattern of oxycodone form II expressed in terms of °2θ.

FIG. 5. is an X-ray powder diffraction pattern of oxycodone form III expressed in terms of °2θ.

FIG. 6. is an X-ray powder diffraction pattern of oxycodone form IV expressed in terms of °2θ.

FIG. 7. is an X-ray powder diffraction pattern of oxycodone form V expressed in terms of °2θ.

FIG. 8. is an X-ray powder diffraction pattern of oxycodone form VI expressed in terms of °2θ.

FIG. 9. is an X-ray powder diffraction pattern of oxycodone form VII expressed in terms of °2θ.

FIG. 10. is an X-ray powder diffraction pattern of oxycodone form VIII expressed in terms of °2θ.

Table I summarizes the prominent peaks of the X-ray powder diffraction patterns of each oxycodone form. The relative intensity (R.I.) of each peak is shown, wherein R.I. is the ratio of the height of each peak compared to the highest peak, which is designated as 100%.

The data were generated using either:
1) a Shamadzu XRD-6000 X-ray powder diffractometer using Cu Kα radiation, fitted with a fine-focus X-ray tube, set at 40 kV and 40 mA. The divergence and scattering slits were set at 1° and the receiving slit was set at 0.15 mm. Diffracted radiation was detected by a NaI scintillation detector. A theta-two theta continuous scan was used at 3°/min (0.4 sec/0.02° step) from 2.5 to 40 °2θ; or
2) an Inel XRG-300 X-ray powder diffractometer using Cu Kα radiation, fitted with a curved position-sensitive detector, set at 40 kV and 30 mA. Data were collected in real time over a 2-theta range of 120° at a resolution of 0.03°. Samples were packed in a capillary x-ray tube and analyzed with the tube spinning.

TABLE I

OXYCODONE ° 2θ PEAKS AND RELATIVE INTENSITIES

| Oxy | R.I. | A | R.I. | I | R.I. | II | R.I. | III | R.I. |
|---|---|---|---|---|---|---|---|---|---|
| 8.35 | 43 | 7.52 | 14 | 7.26 | 100 | 6.96 | 23 | 7.44 | 62 |
| 10.75 | 40 | 7.87 | 76 | 10.68 | 14 | 7.51 | 80 | 7.52 | 58 |
| 12.10 | 100 | 10.36 | 12 | 11.81 | 74 | 10.75 | 77 | 7.74 | 16 |
| 14.00 | 30 | 10.67 | 15 | 13.85 | 19 | 11.77 | 53 | 7.88 | 11 |
| 14.14 | 20 | 11.10 | 19 | 16.21 | 29 | 12.36 | 68 | 11.77 | 17 |
| 16.02 | 25 | 11.64 | 19 | 17.77 | 19 | 13.96 | 23 | 16.25 | 100 |
| 16.24 | 56 | 11.88 | 67 | 20.09 | 13 | 15.11 | 15 | 18.04 | 10 |
| 17.21 | 12 | 13.04 | 24 | 24.90 | 12 | 16.27 | 100 | 20.18 | 10 |
| 17.72 | 35 | 15.88 | 20 | 26.27 | 28 | 17.94 | 57 | 25.28 | 10 |
| 18.26 | 38 | 16.14 | 100 | 27.39 | 11 | 20.13 | 37 | 25.48 | 10 |
| 19.14 | 41 | 17.66 | 16 | 32.41 | 11 | 20.48 | 28 | | |
| 19.46 | 14 | 17.98 | 47 | | | 20.83 | 33 | | |
| 20.16 | 14 | 19.76 | 13 | | | 21.49 | 11 | | |
| 20.29 | 43 | 20.09 | 50 | | | 22.24 | 12 | | |
| 20.72 | 13 | 20.66 | 28 | | | 23.76 | 11 | | |
| 21.60 | 12 | 20.88 | 15 | | | 25.30 | 57 | | |
| 21.81 | 14 | 21.41 | 17 | | | 25.58 | 34 | | |
| 23.54 | 15 | 22.72 | 12 | | | 25.76 | 17 | | |
| 24.04 | 21 | 22.98 | 13 | | | 26.26 | 15 | | |
| 25.22 | 24 | 23.99 | 11 | | | 27.60 | 13 | | |
| 26.09 | 12 | 25.06 | 33 | | | 28.07 | 12 | | |
| 26.87 | 10 | 25.57 | 48 | | | 30.41 | 15 | | |

TABLE I-continued

OXYCODONE ° 2θ PEAKS AND RELATIVE INTENSITIES

| | | | | | |
|---|---|---|---|---|---|
| 28.17 | 19 | 26.17 | 12 | 31.37 | 11 |
| 28.36 | 11 | 28.96 | 30 | 35.93 | 11 |
| 29.01 | 14 | 30.25 | 16 | | |
| 30.02 | 17 | 31.10 | 14 | | |
| 30.18 | 12 | 38.31 | 13 | | |

| IV | R.I. | V | R.I. | VI | R.I. | VII | R.I. | VIII | R.I. |
|---|---|---|---|---|---|---|---|---|---|
| 7.38 | 37 | 6.85 | 19 | 7.31 | 100 | 7.94 | 31 | 10.50 | 13 |
| 10.59 | 51 | 7.16 | 28 | 10.70 | 41 | 8.16 | 55 | 10.81 | 100 |
| 11.84 | 78 | 7.37 | 100 | 11.80 | 51 | 8.40 | 10 | 12.28 | 17 |
| 13.97 | 22 | 11.48 | 30 | 12.48 | 10 | 10.52 | 10 | 12.58 | 64 |
| 14.91 | 12 | 19.47 | 18 | 13.90 | 25 | 10.73 | 21 | 12.72 | 76 |
| 16.01 | 65 | 22.20 | 11 | 14.89 | 16 | 11.24 | 30 | 12.92 | 73 |
| 16.24 | 14 | 22.35 | 15 | 16.30 | 56 | 11.78 | 44 | 13.08 | 57 |
| 17.44 | 36 | | | 17.87 | 49 | 12.02 | 24 | 13.24 | 38 |
| 17.62 | 100 | | | 18.86 | 10 | 12.40 | 48 | 13.42 | 19 |
| 18.19 | 24 | | | 19.85 | 10 | 13.83 | 22 | 14.50 | 15 |
| 19.02 | 10 | | | 20.17 | 30 | 14.00 | 12 | 14.64 | 14 |
| 19.51 | 13 | | | 20.54 | 16 | 15.82 | 11 | 24.04 | 16 |
| 19.95 | 75 | | | 21.48 | 14 | 16.18 | 100 | 24.14 | 22 |
| 20.67 | 14 | | | 21.99 | 16 | 17.64 | 15 | 24.52 | 35 |
| 21.08 | 26 | | | 22.47 | 11 | 18.00 | 14 | 24.64 | 43 |
| 21.31 | 22 | | | 24.47 | 22 | 18.16 | 21 | 24.76 | 24 |
| 21.87 | 12 | | | 25.35 | 11 | 18.88 | 14 | 27.31 | 28 |
| 22.55 | 17 | | | 25.55 | 19 | 19.10 | 14 | 28.17 | 10 |
| 24.34 | 45 | | | 26.40 | 24 | 19.36 | 11 | | |
| 25.11 | 56 | | | 26.65 | 24 | 19.50 | 11 | | |
| 25.36 | 26 | | | 27.56 | 25 | 20.14 | 21 | | |
| 26.58 | 45 | | | 30.68 | 19 | 20.48 | 22 | | |
| 27.32 | 10 | | | 32.56 | 16 | 21.06 | 20 | | |
| 27.59 | 27 | | | 35.12 | 10 | 21.91 | 11 | | |
| 28.01 | 15 | | | 37.84 | 11 | 23.86 | 12 | | |
| 29.36 | 10 | | | | | 24.08 | 32 | | |
| 30.14 | 13 | | | | | 25.04 | 22 | | |
| 30.38 | 34 | | | | | 25.38 | 50 | | |
| 31.20 | 12 | | | | | 25.58 | 29 | | |
| 34.26 | 12 | | | | | 27.89 | 12 | | |
| 34.58 | 11 | | | | | 29.23 | 11 | | |
| 35.35 | 14 | | | | | 30.33 | 21 | | |
| 36.36 | 18 | | | | | | | | |

Table II summarizes the peaks of the X-ray powder diffraction patterns of each oxycodone form that are either unique (peaks that are not shared with other forms within ±0.20 °2θ) or intense (R.I.≧15).

TABLE II

SIGNIFICANT OXYCODONE ° 2θ PEAKS

| A | I | II | III | IV | V | VI | VII | VIII |
|---|---|---|---|---|---|---|---|---|
| 7.87 | 7.26 | 7.51 | 7.44 | 11.84 | 6.85 | 7.31 | 8.16 | 10.81 |
| 11.88 | 11.81 | 10.75 | 7.52 | 16.01 | 7.16 | 11.80 | 12.40 | 12.58 |
| 16.14 | 16.21 | 12.36 | 11.77 | 17.62 | 7.37 | 16.30 | 16.18 | 12.72 |
| 20.09 | 26.27 | 16.27 | 16.25 | 19.95 | 11.48 | 17.87 | 25.38 | 12.92 |
| 22.98 | 32.41 | 35.93 | | 34.26 | | 30.68 | | |
| 38.31 | | | | 34.58 | | 32.56 | | |
| | | | | 35.35 | | 37.84 | | |
| | | | | 36.36 | | | | |

The invention is further defined by reference to the following examples, which are intended to be illustrative and not limiting.

EXAMPLE 1

Preparation of Form A

Oxycodone, 29.8 mg, and 75:25 ethanol/water, 0.8 mL, were combined in a vial, which was sonicated to dissolve the solids. The sample was filtered (0.2 µm nylon filter) and allowed to evaporate uncapped to dryness to yield Form A.

EXAMPLE 2

Preparation of Form I

Oxycodone, 50.0 mg, and water, 0.3 mL, were combined in a vial, which was sonicated to dissolve the solids. The sample was filtered (0.2 µm nylon filter) and allowed to evaporate uncapped to dryness to yield Form I.

EXAMPLE 3

Preparation of Form II

Oxycodone, 199.4 mg, and 95:5 ethanol/water, 2 mL, were combined in a vial to form a cloudy sample, which was agitated at 60° C. The sample was filtered (0.2 µm nylon filter) and allowed to evaporate very slowly, i.e. covered with foil containing 1 pinhole, to yield Form II.

EXAMPLE 4

Preparation of Form III

Oxycodone, 100.5 mg, and ethanol, 1.6 mL, were combined in a vial, which was stirred for approximately 10 min. at 60° C. The sample was filtered (0.2 µm nylon filter) into a clean vial and cooled to 20° C. covered to yield Form III.

EXAMPLE 5

Preparation of Form IV

Oxycodone, 49.8 mg, and dioxane, 18 mL, were combined in a vial to form a cloudy sample, which was stirred at ambient temperature overnight. The resultant solids were collected by vacuum filtration to yield Form IV.

EXAMPLE 6

Preparation of Form V

Oxycodone, 50.0 mg, and 92:8 butanol/water, 3.3 mL, were combined in a vial, which was sonicated to dissolve solids. The sample was filtered (0.2 µm nylon filter) and allowed to evaporate uncapped to dryness to yield Form V.

EXAMPLE 7

Preparation of Form VI

Oxycodone, 50.8 mg, and 92:8 isopropanol/water, 6 mL, were combined in a vial, which was sonicated to dissolve solids. The sample was filtered (0.2 µm nylon filter) and allowed to evaporate very slowly, i.e. covered with foil containing 1 pinhole, to dryness to yield Form VI.

EXAMPLE 8

Preparation of Form VII

Oxycodone Form A was heated to 60-120° C. on a variable temperature XRPD for less than 30 min. to yield Form VII.

EXAMPLE 9

Preparation of Form VIII

Oxycodone was heated to 200° C. on a variable temperature XRPD for less than 30 min. to yield Form VIII.

What is claimed is:

1. Form A of oxycodone.HCl having the following °2θ peaks and relative intensities in X-ray powder diffraction pattern:

| °2θ | R.I. |
|---|---|
| 7.52 | 14 |
| 7.87 | 76 |
| 10.36 | 12 |
| 10.67 | 15 |
| 11.10 | 19 |
| 11.64 | 19 |
| 11.88 | 67 |
| 13.04 | 24 |
| 15.88 | 20 |
| 16.14 | 100 |
| 17.66 | 16 |
| 17.98 | 47 |
| 19.76 | 13 |
| 20.09 | 50 |
| 20.66 | 28 |
| 20.88 | 15 |
| 21.41 | 17 |
| 22.72 | 12 |
| 22.98 | 13 |
| 23.99 | 11 |
| 25.06 | 33 |
| 25.57 | 48 |
| 26.17 | 12 |
| 28.96 | 30 |
| 30.25 | 16 |
| 31.10 | 14 |
| 38.31 | 13. |

2. Form I of oxycodone.HCl having the following °2θ peaks and relative intensities in X-ray powder diffraction pattern:

| °2θ | R.I. |
|---|---|
| 7.26 | 100 |
| 10.68 | 14 |
| 11.81 | 74 |
| 13.85 | 19 |
| 16.21 | 29 |
| 17.77 | 19 |
| 20.09 | 13 |
| 24.90 | 12 |
| 26.27 | 28 |
| 27.39 | 11 |
| 32.41 | 11. |

3. Form II of oxycodone.HCl having the following °2θ peaks and relative intensities in X-ray powder diffraction pattern:

| °2θ | R.I. |
|---|---|
| 6.96 | 23 |
| 7.51 | 80 |
| 10.75 | 77 |
| 11.77 | 53 |
| 12.36 | 68 |
| 13.96 | 23 |
| 15.11 | 15 |
| 16.27 | 100 |
| 17.94 | 57 |
| 20.13 | 37 |
| 20.48 | 28 |
| 20.83 | 33 |
| 21.49 | 11 |
| 22.24 | 12 |
| 23.76 | 11 |
| 25.30 | 57 |
| 25.58 | 34 |
| 25.76 | 17 |
| 26.26 | 15 |
| 27.60 | 13 |
| 28.07 | 12 |
| 30.41 | 15 |
| 31.37 | 11 |
| 35.93 | 11. |

4. Form III of oxycodone.HCl having the following °2θ peaks and relative intensities in X-ray powder diffraction pattern:

| °2θ | R.I. |
|---|---|
| 7.44 | 62 |
| 7.52 | 58 |
| 7.74 | 16 |
| 7.88 | 11 |
| 11.77 | 17 |
| 16.25 | 100 |
| 18.04 | 10 |
| 20.18 | 10 |
| 25.28 | 10 |
| 25.48 | 10. |

5. Form IV of oxycodone.HCl having the following °2θ peaks and relative intensities in X-ray powder diffraction pattern:

| °2θ | R.I. |
|---|---|
| 7.38 | 37 |
| 10.59 | 51 |
| 11.84 | 78 |
| 13.97 | 22 |
| 14.91 | 12 |
| 16.01 | 65 |
| 16.24 | 14 |
| 17.44 | 36 |
| 17.62 | 100 |
| 18.19 | 24 |
| 19.02 | 10 |
| 19.51 | 13 |
| 19.95 | 75 |
| 20.67 | 14 |
| 21.08 | 26 |
| 21.31 | 22 |
| 21.87 | 12 |
| 22.55 | 17 |
| 24.34 | 45 |
| 25.11 | 56 |
| 25.36 | 26 |
| 26.58 | 45 |
| 27.32 | 10 |
| 27.59 | 27 |
| 28.01 | 15 |

| °2θ | R.I. |
| --- | --- |
| 29.36 | 10 |
| 30.14 | 13 |
| 30.38 | 34 |
| 31.20 | 12 |
| 34.26 | 12 |
| 34.58 | 11 |
| 35.35 | 14 |
| 36.36 | 18. |

6. Form V of oxycodone.HCl having the following °2θ peaks and relative intensities in X-ray powder diffraction pattern:

| °2θ | R.I. |
| --- | --- |
| 6.85 | 19 |
| 7.16 | 28 |
| 7.37 | 100 |
| 11.48 | 30 |
| 19.47 | 18 |
| 22.20 | 11 |
| 22.35 | 15. |

7. Form VI of oxycodone.HCl having the following °2θ peaks and relative intensities in X-ray powder diffraction pattern:

| °2θ | R.I. |
| --- | --- |
| 7.31 | 100 |
| 10.70 | 41 |
| 11.80 | 51 |
| 12.48 | 10 |
| 13.90 | 25 |
| 14.89 | 16 |
| 16.30 | 56 |
| 17.87 | 49 |
| 18.86 | 10 |
| 19.85 | 10 |
| 20.17 | 30 |
| 20.54 | 16 |
| 21.48 | 14 |
| 21.99 | 16 |
| 22.47 | 11 |
| 24.47 | 22 |
| 25.35 | 11 |
| 25.55 | 19 |
| 26.40 | 24 |
| 26.65 | 24 |
| 27.56 | 25 |
| 30.68 | 19 |
| 32.56 | 16 |
| 35.12 | 10 |
| 37.84 | 11. |

8. Form VII of oxycodone.HCl having the following °2θ peaks and relative intensities in X-ray powder diffraction pattern:

| °2θ | R.I. |
| --- | --- |
| 7.94 | 31 |
| 8.16 | 55 |
| 8.40 | 10 |
| 10.52 | 10 |
| 10.73 | 21 |
| 11.24 | 30 |
| 11.78 | 44 |
| 12.02 | 24 |
| 12.40 | 48 |
| 13.83 | 22 |
| 14.00 | 12 |
| 15.82 | 11 |
| 16.18 | 100 |
| 17.64 | 15 |
| 18.00 | 14 |
| 18.16 | 21 |
| 18.88 | 14 |
| 19.10 | 14 |
| 19.36 | 11 |
| 19.50 | 11 |
| 20.14 | 21 |
| 20.48 | 22 |
| 21.06 | 20 |
| 21.91 | 11 |
| 23.86 | 12 |
| 24.08 | 32 |
| 25.04 | 22 |
| 25.38 | 50 |
| 25.58 | 29 |
| 27.89 | 12 |
| 29.23 | 11 |
| 30.33 | 21. |

9. Form VIII of oxycodone.HCl having the following °2θ peaks and relative intensities in X-ray powder diffraction pattern:

| °2θ | R.I. |
| --- | --- |
| 10.50 | 13 |
| 10.81 | 100 |
| 12.28 | 17 |
| 12.58 | 64 |
| 12.72 | 76 |
| 12.92 | 73 |
| 13.08 | 57 |
| 13.24 | 38 |
| 13.42 | 19 |
| 14.50 | 15 |
| 14.64 | 14 |
| 24.04 | 16 |
| 24.14 | 22 |
| 24.52 | 35 |
| 24.64 | 43 |
| 24.76 | 24 |
| 27.31 | 28 |
| 28.17 | 10. |

10. Form A of oxycodone.HCl, having the following °2θ peaks in X-ray powder diffraction pattern: 7.87, 11.88, 16.14, 20.09, 22.98, and 38.31.

11. Form I of oxycodone.HCl, having the following °2θ peaks in X-ray powder diffraction pattern: 7.26, 11.81, 16.21, 26.27, and 32.41.

12. Form II of oxycodone.HCl, having the following °2θ peaks in X-ray powder diffraction pattern: 7.51, 10.75, 12.36, 16.27, and 35.93.

13. Form III of oxycodone.HCl, having the following °2θ peaks in X-ray powder diffraction pattern: 7.44, 7.52, 11.77, and 16.25.

14. Form IV of oxycodone.HCl, having the following °2θ peaks in X-ray powder diffraction pattern: 11.84, 16.01, 17.62, 19.95, 34.26, 34.58, 35.35, and 36.36.

15. Form V of oxycodone.HCl, having the following °2θ peaks in X-ray powder diffraction pattern: 6.85, 7.16, 7.37, and 11.48.

16. Form VI of oxycodone.HCl, having the following °2θ peaks in X-ray powder diffraction pattern: 7.31, 11.80, 16.30, 17.87, 30.68, 32.56, and 37.84.

17. Form VII of oxycodone.HCl, having the following °2θ peaks in X-ray powder diffraction pattern: 8.16, 12.40, 16.18, and 25.38.

18. Form VIII of oxycodone.HCl, having the following °2θ peaks in X-ray powder diffraction pattern: 10.81, 12.58, 12.72, and 12.92.

19. A form of claim 1 which is 90-100% pure (wt./wt.).

20. A form of claim 19 which is 95-100% pure.

21. A form of claim 19 which is 98-100% pure.

22. A process for making a compound of claim 1 which comprises: combining oxycodone and 75:25 ethanol/water, sonicating to dissolve the solids, filtering said combination, and allowing said combination to evaporate uncapped to dryness to yield Form A.

23. A process for making a compound of claim 2 which comprises: combining oxycodone and water, sonicating to dissolve the solids, filtering said combination, and allowing said combination to evaporate uncapped to dryness to yield Form I.

24. A process for making a compound of claim 3 which comprises: combining oxycodone and ethanol/water, agitating said combination at 60° C., filtering said combination, and allowing said combination to very slowly evaporate to dryness to yield Form II.

25. A process for making a compound of claim 4 which comprises: combining oxycodone and ethanol, agitating said combination at 60° C., filtering said combination, and cooling said combination to 20° C. covered to yield Form III.

26. A process for making a compound of claim 5 which comprises: combining oxycodone and dioxane, and agitating said combination at ambient temperature overnight to yield Form IV.

27. A process for making a compound of claim 6 which comprises: combining oxycodone and 92:8 butanol/water, sonicating to dissolve the solids, filtering said combination, and allowing said combination to evaporate uncapped to dryness to yield Form V.

28. A process for making a compound of claim 7 which comprises: combining oxycodone and 92:8 isopropanol/water, sonicating to dissolve the solids, filtering said combination, and allowing said combination to evaporate very slowly to dryness to yield Form VI.

29. A process for making a compound of claim 8 which comprises: heating Form A to 60-120° C. for less than 30 min. to yield Form VII.

30. A process for making a compound of claim 9 which comprises: heating oxycodone to 200° C. for less than 30 min. to yield Form VIII.

31. A form of claim 2 which is 95-100% pure (wt./wt.).
32. A form of claim 31 which is 98-100% pure.
33. A form of claim 3 which is 95-100% pure (wt./wt.).
34. A form of claim 33 which is 98-100% pure.
35. A form of claim 4 which is 95-100% pure (wt./wt.).
36. A form of claim 35 which is 98-100% pure.
37. A form of claim 5 which is 95-100% pure (wt./wt.).
38. A form of claim 37 which is 98-100% pure.
39. A form of claim 6 which is 95-100% pure (wt./wt.).
40. A form of claim 39 which is 98-100% pure.
41. A form of claim 7 which is 95-100% pure (wt./wt.).
42. A form of claim 41 which is 98-100% pure.
43. A form of claim 8 which is 95-100% pure (wt./wt.).
44. A form of claim 43 which is 98-100% pure.
45. A form of claim 9 which is 95-100% pure (wt./wt.).
46. A form of claim 45 which is 98-100% pure.
47. A form of claim 10 which is 95-100% pure (wt./wt.).
48. A form of claim 47 which is 98-100% pure.
49. A form of claim 11 which is 95-100% pure (wt./wt.).
50. A form of claim 49 which is 98-100% pure.
51. A form of claim 12 which is 95-100% pure (wt./wt.).
52. A form of claim 51 which is 98-100% pure.
53. A form of claim 13 which is 95-100% pure (wt./wt.).
54. A form of claim 53 which is 98-100% pure.
55. A form of claim 14 which is 95-100% pure (wt./wt.).
56. A form of claim 55 which is 98-100% pure.
57. A form of claim 15 which is 95-100% pure (wt./wt.).
58. A form of claim 57 which is 98-100% pure.
59. A form of claim 16 which is 95-100% pure (wt./wt.).
60. A form of claim 59 which is 98-100% pure.
61. A form of claim 17 which is 95-100% pure (wt./wt.).
62. A form of claim 61 which is 98-100% pure.
63. A form of claim 18 which is 95-100% pure (wt./wt.).
64. A form of claim 63 which is 98-100% pure.

* * * * *